(12) United States Patent
Von Kalle et al.

(10) Patent No.: US 6,514,706 B1
(45) Date of Patent: Feb. 4, 2003

(54) LINEAR AMPLIFICATION MEDIATED PCR (LAM PCR)

(76) Inventors: Christoph Von Kalle, Scheuerleweg 11 f, D-79227 Schallstadt (DE); Manfred Schmidt, Klarastrasse 12, D-79106 Freiburg (DE)

(*) Notice: Subject to any disclaimer, the term of this patent is extended or adjusted under 35 U.S.C. 154(b) by 0 days.

(21) Appl. No.: 09/830,337
(22) PCT Filed: Oct. 26, 1999
(86) PCT No.: PCT/EP99/08077
§ 371 (c)(1), (2), (4) Date: Jul. 16, 2002
(87) PCT Pub. No.: WO00/24929
PCT Pub. Date: May 4, 2000

(30) Foreign Application Priority Data

Oct. 26, 1998 (DE) .......................... 198 49 318

(51) Int. Cl.[7] .............................. C12Q 1/68; C12P 19/34
(52) U.S. Cl. ............................................ 435/6; 435/91.2
(58) Field of Search ..................................... 435/6, 91.2

(56) References Cited

U.S. PATENT DOCUMENTS

| | | | | |
|---|---|---|---|---|
| 5,104,792 A | * | 4/1992 | Silver et al. | 435/6 |
| 5,599,696 A | | 2/1997 | Mueller et al. | 435/91.2 |
| 5,731,171 A | * | 3/1998 | Bohlander | 435/91.2 |

FOREIGN PATENT DOCUMENTS

| | | |
|---|---|---|
| EP | 0356021 | 2/1990 |
| EP | 0395398 | 10/1990 |
| WO | WO9118114 | 11/1991 |
| WO | WO9213104 | 8/1992 |
| WO | WO9309246 | 5/1993 |
| WO | WO9311261 | 6/1993 |
| WO | WO9312245 | 6/1993 |

OTHER PUBLICATIONS

Nguyen et al., Gene 210, 93–101 (1998).*
Mueller, Paul R. et al., "In vivo footprinting . . . ", Sciece, Research Articles Nov. 1989, vol. 246, pp. 780–786.
Prod 'Hom, Guy et al., "A reliable amplification . . . ", FEMS Microbiology Lettters, (1998) 158, pp. 75–81.
Silver, Jonathan et al., "Novel use of polymerase . . . ", Journal of Virology, May 1989, vol. 63., No. 5, pp. 1924–1928.
Miller, A.D. et al., "Improved retroviral vectors . . . ", Biotechniques, (1989) vol. 7, No. 9, 980–982.

* cited by examiner

Primary Examiner—Kenneth R. Horlick
(74) Attorney, Agent, or Firm—Birch, Stewart, Kolasch & Birch, LLP (57) ABSTRACT

A high sensitive method for identifying and/or sequencing an unknown DNA or RNA sequence flanking a known DNA or RNA region is described, wherein, (a) one or more DNA or RNA fragments are subjected in a first step to one or more linear PCR steps using one more primers, (b) the single strands obtained are complemented to form double strands, (c) the double strands are digested by one or more restriction enzymes in order to produce smooth and/or cohesive ends, (d) an oligonucleotide of known sequence is added at the digested ends, and (e) the thus obtained DNA fragments are amplified and detected.

30 Claims, 4 Drawing Sheets

Fig. 1

Scheme of a preferred embodiment of the LAM PCR of the invention
[i] Linear PCR with a biotinilated, vector-specific oligonucleotide. [ii] "Magnetic capture". [iii] Solid phase hexanucleotide priming. [iv] Solid phase restriction digestion. [v] Solid phase ligation followed by alkaline denaturation. [vi] 1st and 2nd exponential PCR of the non-biotinilated DNA strand, for instance by nested PCR. LTRI: Primer for linear PCR, which binds to the known sequence, for instance a retroviral LTR; LC: linker cassettes; LC1, LC2, LTRII, LTRIII: primer for "nested"

Fig. 2

Southern Blot of an in vivo clonal analysis of the peripheral blood of an CML patient (example 1)

LAM-PCR-analysis of 1 µg DNA each at different times after re-infusion. d8, d13 ... d124: 8, 13, ..., 124 days after transplantation, d-7: 7 days before re-infusion (negative patient control) +K: 20 pg of DNA Hela clone 8 + 1 µg of non-transduced Hela DNA (positive control); M: DIG marker VIII.

Fig. 3

High resolution gel electrophoresis (Spreadexgel EL 1200) of an in vivo clonal analysis of peripheral blood of a Rhesus monkey (Example 2)
LAM-PCR analysis of 10 ng and 100 ng DNA each from granulocytes and mononuclear cells 180 days after transplantation (*): 40 μl of concentrated (80%) analysis product, G: granulocytes. MNC: Mononuclear cells. M: 100 bp ladder

Fig. 4

| 5'LTR Flanke | Datum | Fraktion | Sequenz | Sequenz-länge |
|---|---|---|---|---|
| 1774 | 09.03.99 | G | GCTCNNTAATGATTACTTGCATGCCCCGCCTGAAAGACCC | 38 |
| 1775 | 09.03.99 | MNC | ATTNTCCTGCCTCAGCGTNATGGGTAGCTGTGAAAGACCC | 133 |
| 1777 | 09.03.99 | MNC | CTATCATTATTGTCTATTATTATTATTGCTATTGAAAGACCC | 98 |
| 2078 | 17.03.99 | MNC | TGGTTCTGGGTCCTGTCAGCACTCTGAGAGTGAAAGACCC | 150 |
| 2080 | 17.03.99 | MNC | GCAGATGGAACAGCTAAGGCCAAGGGCGGATGAAAGACCC | 186 |
| 2081 | 17.03.99 | MNC | AATTTAAAGGCTCCCCTGTTTGAAAGACCC | 20 |
| 2082/1778 | 17.03.99 | MNC/G | CACGTCCATGGAAGGGGCATGGGCAAGTGATGAAAGACCC | 378 |
| 2083 | 17.03.99 | MNC | GTAACTCGCTGATCATTGATTCATTGATAATGAAAGACCC | 62 |
| 2084 | 17.03.99 | G | AATTACTGAAAGACCC | 6 |
| 2087 | 17.03.99 | MNC | ACTACCTTAGAGAACTGTCCTGTTAAGGGTTGAAAGACCC | 222 |
| 2202 | 19.03.99 | MNC | CCATCTGCTTGGGGAACCTGAGAATCACCTTGAAAGACCC | 65 |
| 2206 | 19.03.99 | MNC | GACCTGTCTCAAAAAGAAAATGTAGCGCCTCTGAAAGACCC | 132 |
| 2209 | 19.03.99 | G | TTTTTTTTTTTTAGAGATGGGGTTTTACCATGAAAGACCC | 108 |
| 2494 | 30.03.99 | G | GAACCTNCCTGANGATTGCTTAAGNGANACTGAAAGACCC | 61 |
| 2498 | 30.03.99 | G | AATTTTTTCATGTCATTTTGCTGTGCCTGAAAGACCC | 27 |
| 2501 | 30.03.99 | G | AATTTCGAGGCTCGTGTTGAAAGACCC | 17 |
| 2502 | 30.03.99 | MNC | ATTGGCTTTAAGCCCAGAGGGTGTAGGTTGTGAAAGACCC | 31 |
| 2861 | 12.04.99 | G | TGATGAGTAAATATCACACACGGGTGAGGAGTGAAAGACCC | 508 |
| 2864 | 12.04.99 | MNC | GTTCACACACCAGAGTCAGGATGCCAGGTCTGAAAGACCC | 320 |
| 2868 | 12.04.99 | G | AGATACAGAGAATATGGAGGAAGAGAAGTTATGAAAGACCC | 79 |
| 2872 | 12.04.99 | MNC | CCAGGTNTNGGCCCTCAGGNNGNGTCGGATXTGAAAGACCC | 102 |
| 3096 | 20.04.99 | G | NNGTGNTGTCATNNTTCAATGNNTGCNGNTTTGAAAGACCC | 388 |
| 3097 | 20.04.99 | G | CCNCGTCCTTGNAAAAGGCTTGGNNAAGGNTGAAAGACCC | 379 |
| 3103 | 20.04.99 | G | AATTCTGAGGTGATATTGAAAGACCC | 16 |
| 3194 | 22.04.99 | MNC | TATAGCGAAACTGAGGCGTTAAGCAAGGCCTGAAAGACCC | 521 |
| 3204 | 22.04.99 | MNC | AGGCATGNAAAGATNCATAACTGACACTAGTGAAAGACCC | 325 |
| 3390 | 27.04.99 | G | ACACTGNNCACTCCAAACATGCTACTCTAGTATTGAAAGACCC | 146 |
| 3392 | 27.04.99 | G | GCCAGGCCTGCACCCTCATAGCGTGGAGAATGAAAGACCC | 449 |
| 3394 | 27.04.99 | G | GCTGCAGACTTTCNTTACTCCNTTAGGTTGTGAAAGACCC | 321 |
| 3397 | 27.04.99 | G | TTTGNCTTTAAANTNANNCTNAGAGGTCAATGAAAGACCC | 255 |
| 3400 | 27.04.99 | G | TCTCTNNAAGNTTCNAGGANGNGNGGGGATTGAAAGACCC | 159 |
| 3408 | 27.04.99 | MNC | AAANCNAAGGGACAGGCTGNAAANGAACCCTGAAAGACCC | 339 |
| 3412 | 27.04.99 | MNC | CCAGCATGAGATCCCCGCGCTGGAGGATCATGAAAGACCC | 575 |
| 3415 | 27.04.99 | MNC | AAAAANGGCCNTTTTTTNGCTAGCNAGGNCTGAAAGACCC | 405 |
| 3417 | 27.04.99 | MNC | NTNTTATTTGNTCANCTATTAAGCGGTTTTTGAAAGACCC | 242 |
| 3419 | 27.04.99 | MNC | TCTCAAGGGCACCAACATGTAACTGNTGGCTGAAAGACCC | 195 |
| 3421 | 27.04.99 | MNC | GNCNTCTGNGTNNCCCNCGNGNCAGNTNTATGAAAGACCC | 141 |
| 3715 | 07.05.99 | G | ACACTGAAAACTCCAAAGATGCTATTNTATTGAAAGACCC | 172 |
| 3717 | 07.05.99 | G | AATTTAGGGNTCCCNNNNGGNTCGTNCTGAAAGACCC | 27 |
| 3720 | 07.05.99 | G | TTGTGGGNTNNNGGGCNTNTTANGGNGTTNATGAAAGACCC | 212 |
| 3725 | 07.05.99 | G | TGTTTTGTTTNGTTTTGAGACTGAGTCTTGCTGAAAGACCC | 70 |
| 3997 | 17.05.99 | MNC | GANGCNATCAACTANGATGACATACAAAATNTTGAAAGACCC | 84 |
| 4000 | 17.05.99 | MNC | TTTATACATACCCTAGTTTGAGGCCGTTANGCTGAAAGACCC | 528 |
| 4004 | 17.05.99 | MNC | GGTCCNNTNTTTCGNTCCNNNNNNTANGTTATGAAAGACCC | 133 |
| 4006 | 17.05.99 | MNC | GCCNCNGGCNTNNCANTCNCTGGNNCGNGGTGAAAGACCC | 48 |

Rhesus monkey model: DNA sequence analysis of retroviral 5' LTR integration flanks

Representation of 40 nucleotides of the 5'LTR genomic proviral fusion sequence. The DNA sequence of the first 10 nucleotides of the 5'LTR region of the proviral DNA are underscored, said nucleotides being read in the 5'-3' direction. G: granulocytes, MNC: mononuclear cells.

LINEAR AMPLIFICATION MEDIATED PCR (LAM PCR)

This application is the national phase under 35 U.S.C. § 371 of PCT International Application No. PCT/EP99/08077 which has an International filing date of Oct. 26, 1999, which designated the United States of America.

The invention relates to a highly sensitive method for identifying and/or sequencing an unknown DNA or RNA sequence flanking a known DNA or RNA region.

The advent of the PCR technique has greatly contributed to DNA amplification and DNA analysis. The use of this method has allowed DNA fragments to be amplified and detected, even if they are present in minor amounts only. Meanwhile, a great number of variants of the PCR technique have come into existence which lend themselves to the solution of the most different problems. However, known methods have the disadvantage of allowing the detection, characterization and definition of unknown DNA regions which may be of viral, transgenic or genomic origin, to be carried out to a limited degree only.

In the PCR technique in its most general form, a DNA fragment is cleaved into its two strands, two primers are then added, one of which binds to the one end of the strand and the other one of which binds to the other end of the other strand, and both strands are then complemented, using a polymerase. This results into double strands again which can be cleaved again and used for amplification. In this manner, DNA can be exponentially amplified. However, in order for this reaction to be carried out, the two ends of DNA must be known so as to allow the provision of corresponding primers. However, this is often not the case, in particular if insertion sites and integration sites, transposons, transgene regions and the like are to be detected.

For the amplification of nucleotide fragments, the sequence of which is only known in part, different PCR variants have been proposed. One variant, called inverse PCR (Silver and Keerikatte, J. Virol, 63 (1989), 1924–1928) consists in so digesting the DNA by restriction enzymes that sticky ends result which are cycled to form a ring, this ring DNA then being amplified. In this case, two primers can be used which are complementary to the known portion of the sequence and only differ in orientation.

Another variant of the amplification of DNA fragments, the sequence of which is only known in part, is an LM PCR (ligation mediated PCR; Moller and Wold, Science 246 (1989) 780–786). The DNA is so digested with restriction enzymes that blunt ends result, A linker cassette of known sequence is then added to the end of the unknown DNA fragments. This method is carried out with linker cassettes consisting to two non-phosphorylated oligonucleotides and only having a blunt end because of the different lengths of the fragments. Ligation directed in this way only occurs between the linker cassette and the unknown end of the target DNA. The PCR can also be carried out with a primer capable of binding to this linker, and with another primer capable of binding to the known portion of the DNA sequence.

Such a method is for instance described by Guy Prod'hom et al. in "A Reliable Amplification Technique for the Characterization of Genomic DNA Sequences Flanking Insertion Sequences", FEMS Microbiology, Letters, 158 (1998) 75 to 81. For this purpose, DNA containing a gene to be amplified is digested before the PCR technique is carried out, a double stranded linker is then so ligated to the digestion site that the linker remains stable under ligation conditions, but is cleaved in each case from one end of each of the two single strands under PCR conditions after cleavage of the double strand and is then not re-ligated either. A primer which is complementary to the beginning of the known sequence is then added and allows a double strand to form. As this primer can only bind to one strand, only one of the two strands is doubled, The newly synthesized DNA is then used in the subsequent PCR cycles as a template, with two primers being then used, i.e. first the primer which has been used in the first step and which specifically binds to the known DNA, and second a primer which binds to the linker. In this manner, the DNA fragment containing the gene searched for is amplified.

This method also suffers from the drawbacks of low sensitivity and specificity because of losses during preparation. The known methods do not allow single or multiple insertion flanks to be characterized individually and/or within a complex DNA mixture.

It is therefore an object of the present invention to provide a highly sensitive method for individually detecting, characterizing and defining unknown DNA and RNA regions which may be of viral, transgenic or genomic origin and flank known sequences.

This object is attained by a method for detecting a DNA or RNA sequence only known in part, the method comprising the steps of (a) subjecting in a first step one or more DNA or RNA fragments to one or more linear PCR steps using one or more primers, (b) complementing the single strands obtained to form double strands, (c) digesting the double strands by one or more restriction enzymes in order to produce smooth and/or cohesive ends, (d) adding a single stranded or double stranded oligonucteotide of known sequence to the digested ends, and (e) amplifying and detecting the thus obtained DNA fragments by known methods.

Consequently, the method of the invention is carried out using a PCR technique.

Figure 1:
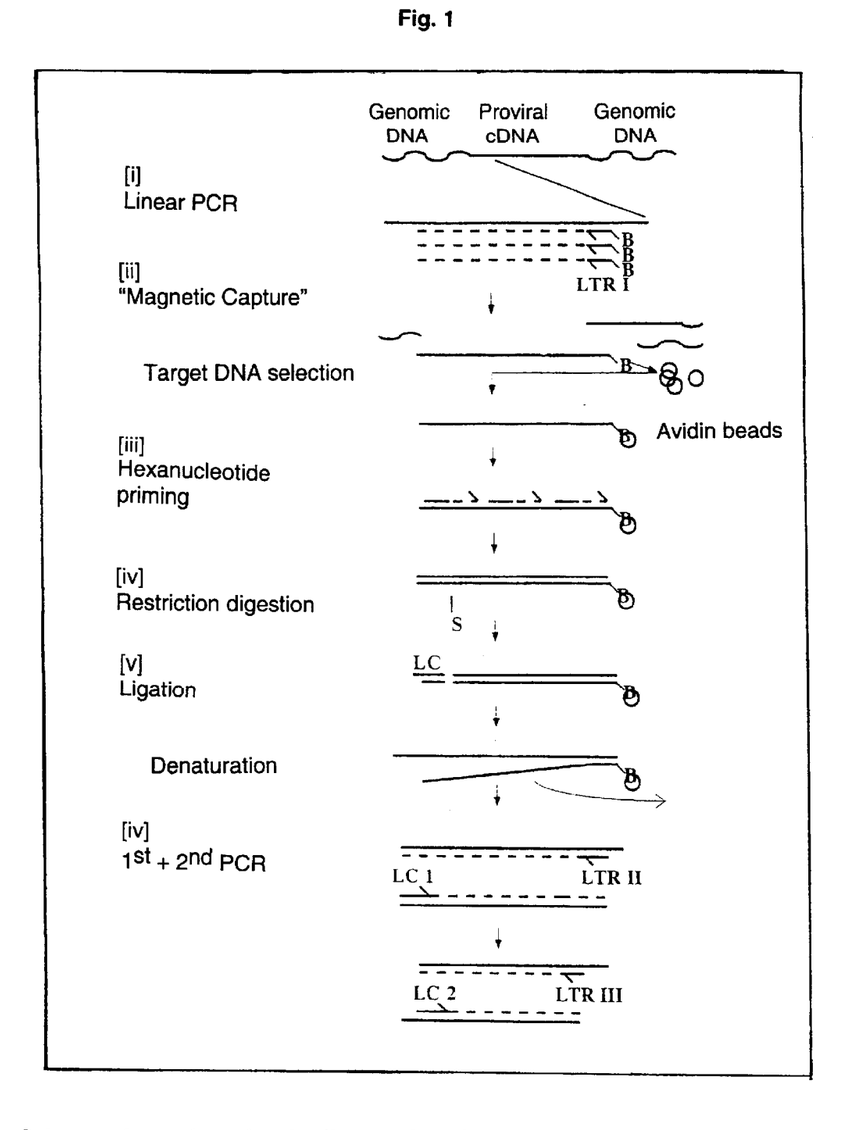
FIG. 1 Scheme of a preferrd embodiment of the LAM PCR of the invention

Step (c) is preferably so carried out that digestion does not occur within a known portion of the target DNA sequence; see for instance step (v) in FIG. 1.

The principle of the invention resides in that the target sequence is linearly amplified by a specific oligonucleotide immediately upon release of the DNA or RNA from one or more cells. In this step, only one primer, which binds to the known part of the nucleotide sequence to be amplified, is used.

The selected primer anneals to the known DNA or RNA sequence, complementary nucleotide units anneal thereto and are bound to each other via a thermostable DNA polymerase. DNA-dependent DNA polymerases (for instance Taq-DNA-polymerase, Pfu-DNA polymerase) are used for DNA sequences, RNA-dependent DNA polymerases (for instance reverse transcriptase) are used for RNA sequences. This reaction step, that is to say construction of a complementary strand, is repeated many times, for instance 10 to 100 times, in particular 30 to 70 times. The sequence of the thus formed DNA strands is composed of the known DNA region and the unknown DNA region following it. Contrary to conventional PCR methods for exponentially amplifying nucleic acids, the method of the invention uses only one primer in the first step. After these linear PCR steps have been carried out, the reaction mixture is purified, in order to allow the next preparative step to take place.

This purification can be achieved in a known manner, for instance by extraction according to Hirt, precipitation with EtOH, use of a silica matrix or glass beads or concentration steps.

However, in order to increase the sensitivity and specificity of the method, separation is preferably carried out by means of a specifically binding pair. In this process. the primer used in the first step carries bound to it a partner of a specifically binding pair, and after termination of the linear PCR the single strands (=target DNA) are separated by means of the second specifically binding partner.
Consequently, in a preferred embodiment of the method (a) one or more DNA fragments or RNA fragments are subjected in a first step to one or more linear PCR steps using one or more primers, wherein the primer(s) is/are provided with a partner of a specifically binding pair, (b) the single stranded fragments carrying the first binding partner are separated from the reaction mixture by means of the second partner of the specifically binding pair, (c) the single strands obtained are complemented to form double strands, (d) the double strands are digested by one or more restriction enzymes in order to produce smooth and/or cohesive ends, (e) a single or double stranded oligonucleotide of known sequence is added to the digested ends, and (f) the thus obtained DNA fragments are multiplied and detected by known methods.

Step (d) is preferably carried out in such a way that digestion does not occur within the known portion of the target DNA sequence, see for instance step (v) of FIG. 1.

This preferred embodiment is carried out with a primer having a partner of a specifically binding pair, the other partner of the specifically binding pair being used to separate the strands from the reaction solution.

After linear amplification of the target sequence, the strand provided with a partner of a specifically binding pair is separated by addition of the other partner of the specifically binding pair, the second partner used for separation, being preferably immobilized on beads, a column matrix or the flask surface coating.

Specifically binding pairs are widely known in the biotechnological field. The best known and most frequently used pair is the combination of biotin and avidin or streptavidin. In a preferred embodiment, the primer is, therefore, biotinilated and avidin or streptavidin is used after having been immobilized on beads or the flask surface. In an especially preferred embodiment, the beads which have the avidin or streptavidin immobilized on them, are magnetic and therefore can be separated from the solution even more easily.

The strand carrying the biotinilated primer is removed from the reaction mixture by means of the immobilized partner and is freed from the unreacted compounds. It is preferred to use several washing steps in the usual manner.

The target DNA immobilized by the specifically binding pair can then be further treated in a solid phase bound form, in order for an exponential PCR to be ultimately carried out for detection. For this purpose, the strands are first complemented to form double strands. This can be done by hexanucleotide priming. In this process, a mixture of different hexanucleotides differing in the nucleotide composition and annealing to complementary sequences of the target nucleotide sequence is used. The double strand is complemented by a polymerase (for instance Klenow polymerase). A possible alternative to hexanucleotide priming consists in the direct application of degenerated primers, a mixture of primers differing in the nucleotide sequences (for instance 20'mers). The completion of the double strands is followed by the digestion of the nucleotide sequences by appropriate restriction enzymes in order for smooth and/or cohesive ends to be produced. The restriction enzymes are preferably so chosen that digestion does not occur within the known part of the target DNA sequence. Restriction enzymes having a recognition and cleavage sequence of 4 base pairs ("four cutters") are preferably used. These enzymes ensure a relatively short fragment length, as they theoretically digest all $4^4$=256 base pairs of the genome. Short lengths of the DNA fragments make the subsequent reaction steps more efficient.

Consequently, the target DNA is now delimited by the known, undigested end and the unknown, digested end. A linker cassette of known sequence can then be added to the digested end of the target DNA. Another possibility is to carry out polynucleotide tailing. In this step, identical nucleotides are added at the 3' end of the target DNA by means of a specific enzyme (for instance poly(A) tailing). The thus obtained double strand, that is to say the thus modified target DNA can then be amplified in the usual manner in a PCR process. On both of its sides, it has a known sequence for which primers can then be provided.

In a preferred embodiment, the double strands containing the target DNA are provided at one or both ends with a double stranded oligonucleotide, the nucleotide sequence of which is known. Examples of suitable oligonucleotides are linker cassettes. Instead of the addition of oligonucleotides, poly(A, T, G or C)tailing can be carried out. The strands are then denatured in a known manner, that is to say are cleaved into single strands, and then a first exponential amplification of the DNA strands is carried out. For this purpose, at least two primers are used, one of which binds to the known portion of the target DNA, while the other one is complementary to the oligonucleotide of known sequence.

Following this amplification, either additional exponential PCR steps, optionally with the use of other primers, can be carried out, or the DNA can be examined by diagnostic methods known per se. Further exponential PCR steps are preferably carried out using nested primers which, based on the position of the primers of the previous PCR, bind within the DNA sequence of the first PCR product. The DNA is preferably further examined by gel electrophoresis, sequencing or blotting. These methods are known to a skilled person and need not be explained in more detail here.

The use of linear amplification in the first reaction step has been found to lead to the amplification of the starting material in the first reaction step and to compensate for any losses in the subsequent preparative steps. In a fifty-fold amplification of the target sequence as much as 98% of the subsequently occurring losses can be compensated for. The method of the invention surprisingly allows an unexpectedly high sensitivity and specificity to be achieved, which could not have been expected from a combination of the individual steps. The specific separation of the target DNA carried out in the second step of the preferred embodiment also additionally enhances the sensitivity and selectivity of the method of the invention, as the background noise can be substantially reduced by separation via specifically binding pairs.

The method of the invention allows a so far unprecedented sensitivity and specificity to be achieved. Moreover, the method of the invention is extraordinarily suited to amplify and analyze DNA fragments, the sequence of which is only known in part.

The combination of linear amplification, specific selection and amplification steps allows a sensitivity and specificity not attainable by other methods to be achieved, Moreover, the possibility of simultaneous detection of multiple insertion flanks within one reaction mixture results in enormous savings of costs and time.

The LAM-PCR method provided according to the present invention can be applied by selection of specific primers simply to any target sequence, whether it is of transgenic, viral, retroviral or genomic origin. The high resolution power allows multiple insertion flanks within a sample to be screened fast by smallest DNA amounts.

The method of the invention also allows labelling studies and studies for gene therapy to be carried out. It allows not only to make clonal analyses, but also to take purely instantaneous pictures, for instance in haematopoietic re-population following transplantation, in competition between retrovirally labelled cells of the transplant and cells that have remained in the body, and it allows cell series and cell generations to be traced, for instance in haematopoiesis. Moreover, it allows preferred integration sites of retro and lentiviruses ("Target Site Selection") to be analyzed. The method of the invention is also a suitable selection method for detecting transciptionally active regions and for analysing different substances for promoting or inhibiting retroviral integration.

The method also lends itself for the examination of transposons in insertion mutagenesis and for "bacterial strain typing" for instance in Mycobacterium tuberculosis, Transgenic plants and animals can also be examined. The method is also suitable to localize resistance genes in culture plants and analyze transgenes in young animals without subsequent sacrifice.

The method of the invention has been carried out in the following examples of simultaneous characterization of multiple retroviral integration flanks. In the first place, genomic DNA from Hela cell clones transduced with vector pLN derived from murine leukemia virus was analyzed. 10 pg of genomic DNA per transduced HeLa clone in a mixture of 1 µg of non-transduced genomic DNA equivalent to a DNA amount of 1.5 cells having a diploid genome were sufficient to detect any retroviral integration flanks present. This corresponds to a resolution power higher than 1.001%.

The invention is explained in more detail by the following examples, representing results of in vivo clonal analyses (characterization of the retroviral integration sites) of the peripheral blood carried out by the LAM-PCR method of the invention.

BRIEF DESCRIPTION OF THE DRAWINGS

[i] Linear PCR with a biotinilated, vector-specific oligonuleotide. [ii] "Magnetic capture". [iii] Solid phase haxanucleotide priming. [iv] Solid phase restiction digestion. [v] Solid phase ligation followed by alkaline denaturation. ]vi] 1st and 2nd exponential PCR of the non-biotinilated DNA strand, for instance by nested PCR. LTRI: Primer for liner PCR, which binds to the known sequence, for instance a retrovial LTR: LC: linker cassettes: LC1, LC2, LTRII, LTRIII; primer for "nested".

LAM-PCR-anlysis of 1 µg DNA each at different times after re-infusion, d8, d13 ... d124: 3, 13, ..., 124 days after transplantation, d-7: 7 days before re-infusion (negative patient cotrol) +K: 20 pg of DNA Hela clone 8+1 µg of non-transduced Hela DNA (positive cintrol); M: DIG marker VIII.

LAM-PCR analysis on 10 ng and 100 ng DNA each from granulocytes and mononuclear cells 180 days after transplantation (*): 40 µl of concentrated (80 %) analysis product, G: granulocytes. MNC: Mononuclear cells. M; 100 bµ ladder.

FIG. 4 Rhesus monkey model: DNA sequence analysis of retroviral 5' LTR integration flanks.

Representation of 40 nucleotides of the 5' LTP genomic proviral fusion sequence, The DNA sequence of the first 10 nucleotides of the 5' LTR region of the proviral DNA are underscored, said nucleotides being read in the 5'–3' direction. G: granulocytes, MNC: mononuclear cels.

EXAMPLE 1

Clonal Analysis of Transduced Human Haematopoietic Stem Cells by Characterization of the Retroviral Integration Sites A retroviral integration analysis of transduced haematopoietic cells was carried out in the course of a clinical gene labelling study. Peripheral blood stem cells (PBS) of an CML patient (chronic myeloic leukemia) were transduced with a retroviral vector (pLN; Miller and Rosmann, Biotechniques 7 (1989), 980–982) which is based on MLV (Moloney Murine Leukemia). Following re-infusion of the labelled cells, a fraction each of the peripheral blood was analyzed at different times for the presence of retroviral integration sites.

Southern blot analysis allowed the identity of the DNA fragments found to be confirmed. The methods known to date do not allow such examinations to be carried out. Another analysis and sequencing allows individual harmless and malign stem cell clones to be identified. The analysis was carried out as follows:

Immediately after the release of the DNA from the cells, the target sequences were in the first place linearly amplified (linear PCR) by specific. biotinilated oligonucleotides, see in this respect also the scheme of FIG. 1.

Figure 2:
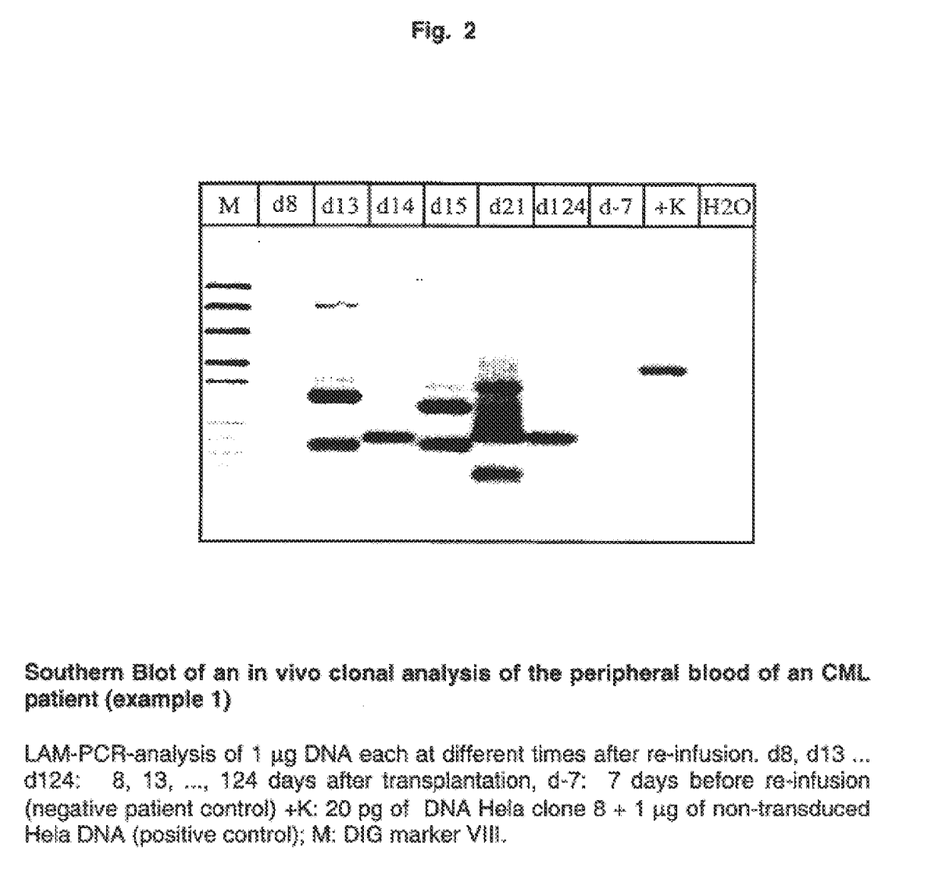
FIG. 2 Southern Blot of an in vivo clonal analysis of the peripheral blood of an CML patient (example 1)

After addition of the primers, the nucleotides and Taq-polymerase, the amplification step was repeated 50 times. Contrary to normal PCR only one primer was used. As the primer was biotinilated, the amplified DNA sequences bound to paramagnetic beads coupled to streptavidin. The strand complementary to the DNA strand coupled to the beads was constructed by means of hexanucleotide priming. The DNA, now double stranded, was digested by the restriction enzyme Sse9l, resulting in the formation of cohesive ends. A so-called linker cassette was annealed to this target DNA and bound by means of a ligase reaction. The linker cassette is an in part double stranded oligonucleotide. The target DNA was subsequently denatured and amplified by the PCR reaction. in this reaction, the primer was so chosen that it anneals to the already known DNA region. The other primer anneals to the linker cassette. In the amplification, 10% of the thus formed product were first subjected to a first PCR comprising 28 cycles, wherein the primer used, deriving from the known DNA region, was added also in biotinilated form. This first PCR product was separated by "Magnetic Capture". A second PCR (=nested PCR) with 28 cycles was carried out with 10% of the product thus formed. 20% of this second PCR product were separated by gel electrophoresis (2% agarose), blotted onto a nylon membrane, hybridized to a digoxigenin-labelled probe, homologous to the known DNA sequence, and detected by chemiluminescence. The results are compiled in FIG. 2. The headings of the individual gel lanes have the following meaning:

M: Digoxigenin-labelled molecular weight standard
d8: 8 days after re-infusion
d13: 13 days after re-infusion
d14: 14 days after re-infusion
d15: 15 days after re-infusion
d21: 21 days after re-infusion
d124: 124 days after re-infusion
d7: 7 days before re-infusion (negative control)
+K: 20 pg of transduced and 1 μg of non-transduced DNA of Hela cells
−K: Control with water After the first amplification, all reaction steps were carried out in the solid phase. Purification between the individual steps was carried out with a magnet. The "used-up" reaction mixture was simply removed by a pipette. This was followed by washing with water once and the reaction mixture required for the next reaction step was then placed into the vessel, This means that all reaction steps up to the first exponential amplification step (first PCR) were carried out in one reaction vessel.

Primers Used:

LC1 (SEQ ID NO: 1): 5'>GACCCGGGAGATCT-GAATTC<3'

LC2 (SEQ ID NO: 2): 5'>GATCTGAATTCAGTGGCA-CAG<3'

LTRI (SEQ ID NO: 3): 5'>AGCTGTTCCATCTGTTC-CTGACCTT<3' (biotinilated at the 5' end)

LTRII (SEQ ID NO: 4): 5'>GGCCTTGATCTGAACT-TCTC<3'

LTRIII (SEQ ID NO: 5): 5'>TTCATGCCTTG-CAAAATGGC<3'

EXAMPLE 2

Clonal Analysis of Transduced Haematopoietic Stem Cells by Characterization of the Retroviral Integration Sites In the Rhesus Monkey Model.

The experiments were carried out as indicated in example 1, however with the following modifications: The retroviral integration analysis was carred out in the Rhesus monkey model.

Figure 3:
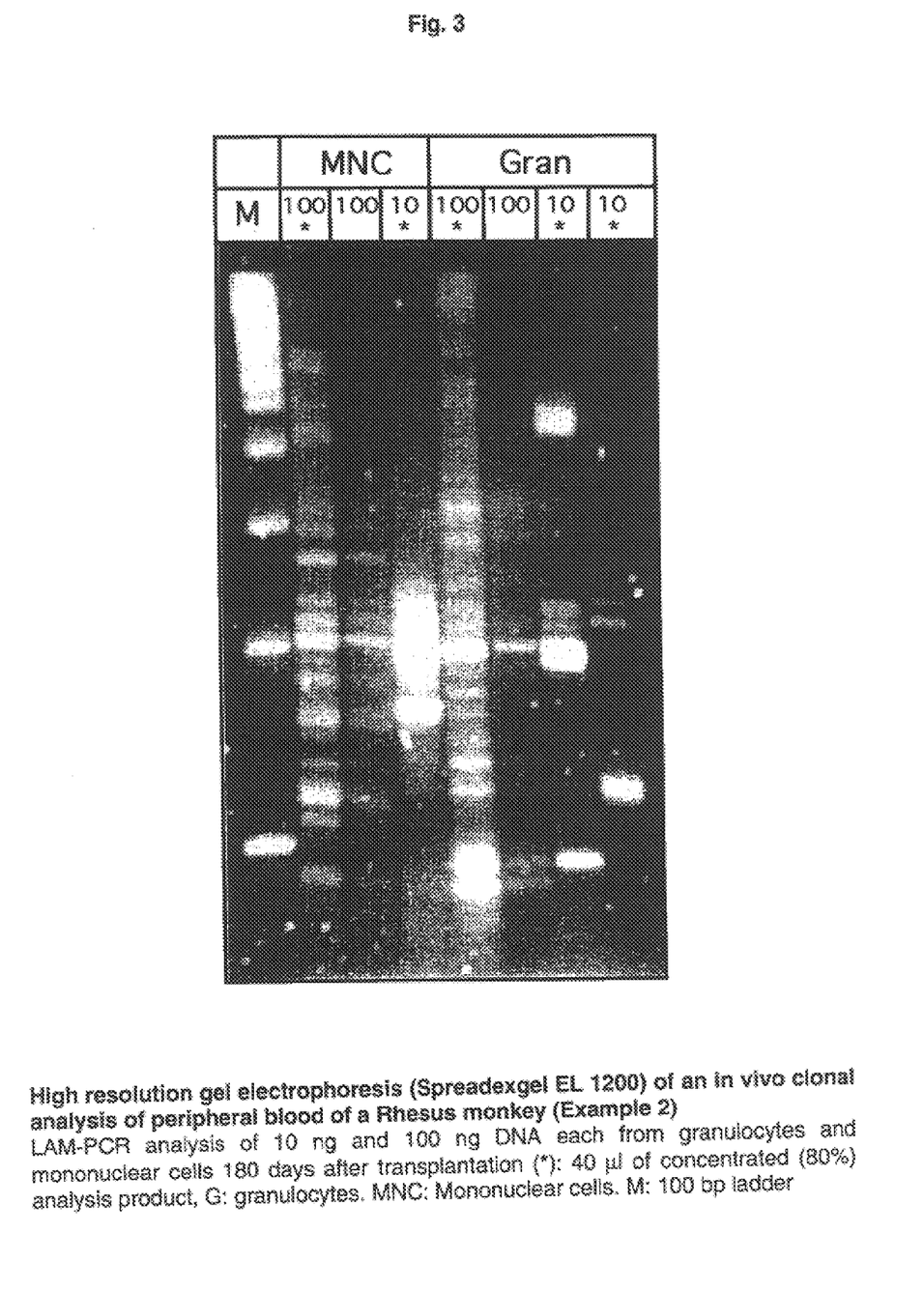
FIG. 3 High resolution gel electrophoresis (Spreadexgel EL 1200) of an in vivo clonal analysis of peripheral blood of a Rhesus monkey (Example 2)

The clonal product achieved was not detected via Southern Blot, but was separated in a high resolution plastic gel, photographically documented via UV light after EtBr staining (FIG. 3), the DNA fragments were isolated from the gel and sequenced (FIG. 4). FIG. 4 shows the retroviral integration sites in altogether 45 different samples (SEQ ID NOS: 6–50).

The same primers as indicated in Example 1 above were used.

What is claimed is:

1. A method for identifying and/or sequencing an unknown or target DNA or RNA sequence flanking a known DNA or RNA region, the method comprising:

(a) subjecting one or more nucleotide sequences in a first step to one or more linear PCR steps using one or more primers to form single strands, (b) complementing or pairing the single strands obtained from step (a) with arbitrary or non-specific priming sequences to form double strands, (c) digesting the double strands with one or more restriction enzymes in order to produce smooth and/or cohesive ends, (d) attaching, annealing or ligating an oligonucleotide of known sequence to the digested ends, and (e) amplifying and detecting the modified DNA fragments.

2. A method for identifying and/or sequencing an unknown or target DNA or RNA flanking a known DNA or RNA sequence, the method comprising:

(a) subjecting one or more DNA or RNA fragments in a first step to one or more linear PCR steps to form single strands, using one or more primers, the primer(s) being provided with a partner of a specific binding pair, said specific binding pair having a first binding partner and a second binding partner, (b) separating the single strand fragments carrying the first binding partner from the reaction mixture by means of the second binding partner of the specific binding pair, (c) complementing or pairing the single strands obtained in step (a) with arbitrary or non-specific priming sequences to form double strands, (d) digesting the double strands with one or more restriction enzymes in order to produce smooth and/or cohesive ends, (e) attaching, annealing or ligating an oligonucleotide of known sequence to the digested ends, and (f) amplifying and detecting the modified DNA fragments.

3. The method according to claim 2, wherein the specific binding pair is selected from the group consisting of biotin and avidin and biotin and streptavidin.

4. The method according to claim 2, wherein one or more primers labelled with biotin are used in step (a) and it (they) is (are) immediately thereafter separated from the reaction mixture by specific binding to avidin or streptavidin.

5. The method according to claim 2, wherein the second partner of the specific bind pair is immobilized on beads or in a coated flask.

6. The method according to claim 1, wherein hexanucleotide primers are used in step (b) to construct the complementary DNA strand.

7. The method according to claim 1, wherein degenerated primers are used in step (b) to construct the complementary DNA strand.

8. The method according to claim 1, the DNA fragments obtained in step (a) is complemented in a solid phase to form double strands.

9. The method according to claim 1, wherein step (c) is carried out in a solid phase.

10. The method according to claim 1, wherein steps 1(d) is carried out in a solid phase and the target DNA is then immediately amplified using a solid phase ligation mediated PCR technique.

11. The method according to claim 1, wherein the oligonucleotide in step 1l(d) is a linker cassette.

12. The method according to claim 1, wherein poly (A, T, G or C) tailing is performed in step 1(d).

13. The method according to claim 11, wherein the target DNA is denatured after step 1(d) and amplified using a PCR technique, the PCR technique being carried out using a primer which is complementary to the linker and a second primer which is complementary to the known DNA region.

14. The method according to claim 13, wherein the target DNA obtained by the first PCR technique is subjected to a second amplification using a nested PCR technique.

15. The method according to claim 13 or 14, wherein the target DNA is detected by gel electrophoresis, blotting or sequencing, after amplification.

16. The method according to claim 1, wherein step (c) is carried out that digestion does not occur within the known part of the target DNA sequence.

17. The method according to claim 16, wherein an oligonucleotide is added only at the digested end.

18. The method according to claim 1 or 2, wherein the genomic localization of transposons, retroviral integration events, retroviral vectors, transcriptionally active regions, resistance genes and/or transgenes is detected, amplified, identified and/or sequenced.

19. The method according to claim 2, wherein hexanucleotide primers are used in step 2(c) to construct the complementary DNA strand.

20. The method according to claim 2, wherein degenerated primers are used in step 2(c) to construct the complementary DNA strand.

21. The method according to claim 2, wherein the DNA fragments from step 2(b) are complemented in a solid phase to form double strands.

22. The method according to claim 2, wherein step 2(d) is carried out in a solid phase.

23. The method according to claim 2, wherein step 2(e) is carried out in a solid phase and the target DNA is immediately amplified using a solid phase ligation mediated PCR technique.

24. The method according to claim 2, wherein the oligonucleotide in step 2(e) is a linker cassette.

25. The method according to claim 2, wherein poly (A, T. G or C) tailing is performed in step 2(e).

26. The method according to claim 24, wherein the target DNA is denatured after step 2(e) and amplified using a PCR technique, the PCR technique being carried out using a primer which is complementary to the linker and a second primer which is complementary to the known DNA region.

27. The method according to claim 26, wherein the target DNA obtained by the first PCR technique is subjected to a second amplification using a nested PCR technique.

28. The method according to claim 26 or 27, wherein the target DNA is detected by gel electrophoresis, blotting or sequencing, after amplification.

29. The method according to claim 2, wherein step 2(d) is carried out so that digestion does not occur within the known part of the target DNA sequence.

30. The method according to claim 29, wherein an oligonucleotide is only added to the digested end.

* * * * *

```
                              SEQUENCE LISTING

<160> NUMBER OF SEQ ID NOS: 50

<210> SEQ ID NO 1
<211> LENGTH: 20
<212> TYPE: DNA
<213> ORGANISM: Artificial Sequence
<220> FEATURE:
<223> OTHER INFORMATION: Description of Artificial Sequence: Primer
      targeted to Homo sapiens

<400> SEQUENCE: 1
gacccgggag atctgaattc                                              20

<210> SEQ ID NO 2
<211> LENGTH: 21
<212> TYPE: DNA
<213> ORGANISM: Artificial Sequence
<220> FEATURE:
<223> OTHER INFORMATION: Description of Artificial Sequence: Primer
      targeted to Homo sapiens

<400> SEQUENCE: 2
gatctgaatt cagtggcaca g                                            21

<210> SEQ ID NO 3
<211> LENGTH: 25
<212> TYPE: DNA
<213> ORGANISM: Artificial Sequence
<220> FEATURE:
<223> OTHER INFORMATION: Description of Artificial Sequence: Primer
      targeted to Homo sapiens
```

<400> SEQUENCE: 3
agctgttcca tctgttcctg acctt                                              25

<210> SEQ ID NO 4
<211> LENGTH: 20
<212> TYPE: DNA
<213> ORGANISM: Artificial Sequence
<220> FEATURE:
<223> OTHER INFORMATION: Description of Artificial Sequence: Primer
      targeted to Homo sapiens

<400> SEQUENCE: 4
ggccttgatc tgaacttctc                                                    20

<210> SEQ ID NO 5
<211> LENGTH: 20
<212> TYPE: DNA
<213> ORGANISM: Artificial Sequence
<220> FEATURE:
<223> OTHER INFORMATION: Description of Artificial Sequence: Primer
      targeted to Homo sapiens

<400> SEQUENCE: 5
ttcatgcctt gcaaaatggc                                                    20

<210> SEQ ID NO 6
<211> LENGTH: 40
<212> TYPE: DNA
<213> ORGANISM: Macaca mulatta
<220> FEATURE:
<221> NAME/KEY: LTR
<222> LOCATION: (31)..(40)
<223> OTHER INFORMATION: The first 10 nucleotides of pLN 5'LTR
      (NCBI/GenBank: M28245)
<223> OTHER INFORMATION: n is a, g, c or t/u

<400> SEQUENCE: 6
gctcnntaat gattacttgc atgccccgcc tgaaagaccc                               40

<210> SEQ ID NO 7
<211> LENGTH: 40
<212> TYPE: DNA
<213> ORGANISM: Macaca mulatta
<220> FEATURE:
<221> NAME/KEY: LTR
<222> LOCATION: (31)..(40)
<223> OTHER INFORMATION: The first 10 nucleotides of pLN 5'LTR
      (NCBI/GenBank: M28245)
<223> OTHER INFORMATION: n is a, g, c, or t/u

<400> SEQUENCE: 7
attntcctgc ctcagcgtna tgggtagctg tgaaagaccc                               40

<210> SEQ ID NO 8
<211> LENGTH: 42
<212> TYPE: DNA
<213> ORGANISM: Macaca mulatta
<220> FEATURE:
<221> NAME/KEY: LTR
<222> LOCATION: (33)..(42)
<223> OTHER INFORMATION: The first 10 nucleotides of pLN 5'LTR
      (NCBI/GenBank: M28245)

<400> SEQUENCE: 8
ctatcattat tgtctattat tattattgct attgaaagac cc                            42

```
<210> SEQ ID NO 9
<211> LENGTH: 40
<212> TYPE: DNA
<213> ORGANISM: Macaca mulatta
<220> FEATURE:
<221> NAME/KEY: LTR
<222> LOCATION: (31)..(40)
<223> OTHER INFORMATION: The first 10 nucleotides of pLN 5'LTR
      (NCBI/GenBank: M28245)

<400> SEQUENCE: 9
tggttctggg tcctgtcagc actctgagag tgaaagaccc                              40

<210> SEQ ID NO 10
<211> LENGTH: 40
<212> TYPE: DNA
<213> ORGANISM: Macaca mulatta
<220> FEATURE:
<221> NAME/KEY: LTR
<222> LOCATION: (31)..(40)
<223> OTHER INFORMATION: The first 10 nucleotides of pLN 5'LTR
      (NCBI/GenBank: M28245)

<400> SEQUENCE: 10
gcagatggaa cagctaaggc caagggcgga tgaaagaccc                              40

<210> SEQ ID NO 11
<211> LENGTH: 30
<212> TYPE: DNA
<213> ORGANISM: Macaca mulatta
<220> FEATURE:
<221> NAME/KEY: LTR
<222> LOCATION: (21)..(30)
<223> OTHER INFORMATION: The first 10 nucleotides of pLN 5'LTR
      (NCBI/GenBank: M28245)

<400> SEQUENCE: 11
aatttaaagg ctcccctgtt tgaaagaccc                                         30

<210> SEQ ID NO 12
<211> LENGTH: 40
<212> TYPE: DNA
<213> ORGANISM: Macaca mulatta
<220> FEATURE:
<221> NAME/KEY: LTR
<222> LOCATION: (31)..(40)
<223> OTHER INFORMATION: The first 10 nucleotides of pLN 5'LTR
      (NCBI/GenBank: M28245)

<400> SEQUENCE: 12
cacgtccatg gaagggcat gggcaagtga tgaaagaccc                               40

<210> SEQ ID NO 13
<211> LENGTH: 40
<212> TYPE: DNA
<213> ORGANISM: Macaca mulatta
<220> FEATURE:
<221> NAME/KEY: LTR
<222> LOCATION: (31)..(40)
<223> OTHER INFORMATION: The first 10 nucleotides of pLN 5'LTR
      (NCBI/GenBank: M28245)

<400> SEQUENCE: 13
gtaactcgct gatcattgat tcattgataa tgaaagaccc                              40

<210> SEQ ID NO 14
<211> LENGTH: 16
<212> TYPE: DNA
<213> ORGANISM: Macaca mulatta
```

```
<220> FEATURE:
<221> NAME/KEY: LTR
<222> LOCATION: (7)..(16)
<223> OTHER INFORMATION: The first 10 nucleotides of pLN 5'LTR
      (NCBI/GenBank: M28245)

<400> SEQUENCE: 14
aattactgaa agaccc                                                        16

<210> SEQ ID NO 15
<211> LENGTH: 40
<212> TYPE: DNA
<213> ORGANISM: Macaca mulatta
<220> FEATURE:
<221> NAME/KEY: LTR
<222> LOCATION: (31)..(40)
<223> OTHER INFORMATION: The first 10 nucleotides of pLN 5'LTR
      (NCBI/GenBank: M28245)

<400> SEQUENCE: 15
actaccttag agaactgtcc tgttaagggt tgaaagaccc                               40

<210> SEQ ID NO 16
<211> LENGTH: 40
<212> TYPE: DNA
<213> ORGANISM: Macaca mulatta
<220> FEATURE:
<221> NAME/KEY: LTR
<222> LOCATION: (31)..(40)
<223> OTHER INFORMATION: The first 10 nucleotides of pLN 5'LTR
      (NCBI/GenBank: M28245)

<400> SEQUENCE: 16
ccatctgctt ggggaacctg agaatcacct tgaaagaccc                               40

<210> SEQ ID NO 17
<211> LENGTH: 41
<212> TYPE: DNA
<213> ORGANISM: Macaca mulatta
<220> FEATURE:
<221> NAME/KEY: LTR
<222> LOCATION: (32)..(41)
<223> OTHER INFORMATION: The first 10 nucleotides of pLN 5'LTR
      (NCBI/GenBank: M28245)

<400> SEQUENCE: 17
gacctgtctc aaaagaaaa tgtagcgcct ctgaaagacc c                              41

<210> SEQ ID NO 18
<211> LENGTH: 40
<212> TYPE: DNA
<213> ORGANISM: Macaca mulatta
<220> FEATURE:
<221> NAME/KEY: LTR
<222> LOCATION: (31)..(40)
<223> OTHER INFORMATION: The first 10 nucleotides of pLN 5'LTR
      (NCBI/GenBank: M28245)

<400> SEQUENCE: 18
tttttttttt ttagagatgg ggttttacca tgaaagaccc                               40

<210> SEQ ID NO 19
<211> LENGTH: 40
<212> TYPE: DNA
<213> ORGANISM: Macaca mulatta
```

```
<220> FEATURE:
<221> NAME/KEY: LTR
<222> LOCATION: ()..()
<223> OTHER INFORMATION: The first 10 nucleotides of pLN 5'LTR
      (NCBI/GenBank: M28245)
<223> OTHER INFORMATION: n is a, g, c or t/u

<400> SEQUENCE: 19
gaacctncct gangattgct taagnganac tgaaagaccc                               40

<210> SEQ ID NO 20
<211> LENGTH: 37
<212> TYPE: DNA
<213> ORGANISM: Macaca mulatta
<220> FEATURE:
<221> NAME/KEY: LTR
<222> LOCATION: (28)..(37)
<223> OTHER INFORMATION: The first 10 nucleotides of pLN 5'LTR
      (NCBI/GenBank: M28245)

<400> SEQUENCE: 20 aatttttca tgtcattttg ctgtgcctga aagaccc                                   37

<210> SEQ ID NO 21
<211> LENGTH: 27
<212> TYPE: DNA
<213> ORGANISM: Macaca mulatta
<220> FEATURE:
<221> NAME/KEY: LTR
<222> LOCATION: (18)..(27)
<223> OTHER INFORMATION: The first 10 nucleotides of pLN 5'LTR
      (NCBI/GenBank: M28245)

<400> SEQUENCE: 21
aatttcgagg ctcgtgttga aagaccc                                             27

<210> SEQ ID NO 22
<211> LENGTH: 40
<212> TYPE: DNA
<213> ORGANISM: Macaca mulatta
<220> FEATURE:
<221> NAME/KEY: LTR
<222> LOCATION: (31)..(40)
<223> OTHER INFORMATION: The first 10 nucleotides of pLN 5'LTR
      (NCBI/GenBank: M28245)

<400> SEQUENCE: 22
attggcttta agcccagagg gtgtaggttg tgaaagaccc                               40

<210> SEQ ID NO 23
<211> LENGTH: 41
<212> TYPE: DNA
<213> ORGANISM: Macaca mulatta
<220> FEATURE:
<221> NAME/KEY: LTR
<222> LOCATION: (32)..(41)
<223> OTHER INFORMATION: The first 10 nucleotides of pLN 5'LTR
      (NCBI/GenBank: M28245)

<400> SEQUENCE: 23
tgatgagtaa atatcacaca cgggtgagga gtgaaagacc c                             41

<210> SEQ ID NO 24
<211> LENGTH: 40
<212> TYPE: DNA
<213> ORGANISM: Macaca mulatta
<220> FEATURE:
<221> NAME/KEY: LTR
<222> LOCATION: (31)..(40)
```

```
<223> OTHER INFORMATION: The first 10 nucleotides of pLN 5'LTR
      (NCBI/GenBank: M28245)

<400> SEQUENCE: 24
gttcacacac cagagtcagg atgccaggtc tgaaagaccc                                40

<210> SEQ ID NO 25
<211> LENGTH: 41
<212> TYPE: DNA
<213> ORGANISM: Macaca mulatta
<220> FEATURE:
<221> NAME/KEY: LTR
<222> LOCATION: (32)..(41)
<223> OTHER INFORMATION: The first 10 nucleotides of pLN 5'LTR
      (NCBI/GenBank: M28245)

<400> SEQUENCE: 25
agatacagag aatatggagg aagagaagtt atgaaagacc c                              41

<210> SEQ ID NO 26
<211> LENGTH: 40
<212> TYPE: DNA
<213> ORGANISM: Macaca mulatta
<220> FEATURE:
<221> NAME/KEY: LTR
<222> LOCATION: (31)..(40)
<223> OTHER INFORMATION: The first 10 nucleotides of pLN 5'LTR
      (NCBI/GenBank: M28245)
<223> OTHER INFORMATION: n is a, g, c or t/u

<400> SEQUENCE: 26
ccaggtntng gccctcaggn ngngtcggat tgaaagaccc                                40

<210> SEQ ID NO 27
<211> LENGTH: 41
<212> TYPE: DNA
<213> ORGANISM: Macaca mulatta
<220> FEATURE:
<221> NAME/KEY: LTR
<222> LOCATION: (32)..(41)
<223> OTHER INFORMATION: The first 10 nucleotides of pLN 5'LTR
      (NCBI/GenBank: M28245)
<223> OTHER INFORMATION: n is a, g, c or t/u

<400> SEQUENCE: 27
nngtgntgtc atnnttcaat gnntgcngnt ttgaaagacc c                              41

<210> SEQ ID NO 28
<211> LENGTH: 40
<212> TYPE: DNA
<213> ORGANISM: Macaca mulatta
<220> FEATURE:
<221> NAME/KEY: LTR
<222> LOCATION: (31)..(40)
<223> OTHER INFORMATION: The first 10 nucleotides of pLN 5'LTR
      (NCBI/GenBank: M28245)
<223> OTHER INFORMATION: n is a, g, c or t/u

<400> SEQUENCE: 28
ccncgtcctt gnaaaaggct tggnnaaggn tgaaagaccc                                40

<210> SEQ ID NO 29
<211> LENGTH: 26
<212> TYPE: DNA
<213> ORGANISM: Macaca mulatta
```

```
<220> FEATURE:
<221> NAME/KEY: LTR
<222> LOCATION: (17)..(26)
<223> OTHER INFORMATION: The first 10 nucleotides of pLN 5'LTR
      (NCBI/GenBank: M28245)

<400> SEQUENCE: 29
aattctgagg tgatattgaa agaccc                                           26

<210> SEQ ID NO 30
<211> LENGTH: 40
<212> TYPE: DNA
<213> ORGANISM: Macaca mulatta
<220> FEATURE:
<221> NAME/KEY: LTR
<222> LOCATION: (31)..(40)
<223> OTHER INFORMATION: The first 10 nucleotides of pLN 5'LTR
      (NCBI/GenBank: M28245)

<400> SEQUENCE: 30
tatagcgaaa ctgaggcgtt aagcaaggcc tgaaagaccc                            40

<210> SEQ ID NO 31
<211> LENGTH: 40
<212> TYPE: DNA
<213> ORGANISM: Macaca mulatta
<220> FEATURE:
<221> NAME/KEY: LTR
<222> LOCATION: (31)..(40)
<223> OTHER INFORMATION: The first 10 nucleotides of pLN 5'LTR
      (NCBI/GenBank: M28245)
<223> OTHER INFORMATION: n is a, g, c or t/u

<400> SEQUENCE: 31
aggcatgnaa agatncataa ctgacactag tgaaagaccc                            40

<210> SEQ ID NO 32
<211> LENGTH: 40
<212> TYPE: DNA
<213> ORGANISM: Macaca mulatta
<220> FEATURE:
<221> NAME/KEY: LTR
<222> LOCATION: (31)..(40)
<223> OTHER INFORMATION: The first 10 nucleotides of pLN 5'LTR
      (NCBI/GenBank: M28245)
<223> OTHER INFORMATION: n is a, g, c or t/u

<400> SEQUENCE: 32
acactgnnca ctccaaacat gctactctat tgaaagaccc                            40

<210> SEQ ID NO 33
<211> LENGTH: 40
<212> TYPE: DNA
<213> ORGANISM: Macaca mulatta
<220> FEATURE:
<221> NAME/KEY: LTR
<222> LOCATION: (31)..(40)
<223> OTHER INFORMATION: The first 10 nucleotides of pLN 5'LTR
      (NCBI/GenBank: M28245)

<400> SEQUENCE: 33
gccaggcctg caccctcata gcgtggagaa tgaaagaccc                            40

<210> SEQ ID NO 34
<211> LENGTH: 40
<212> TYPE: DNA
<213> ORGANISM: Macaca mulatta
<220> FEATURE:
<221> NAME/KEY: LTR
```

<222> LOCATION: (31)..(40)
<223> OTHER INFORMATION: The first 10 nucleotides of pLN 5'LTR
      (NCBI/GenBank: M28245)
<223> OTHER INFORMATION: n is a, g, c or t/u

<400> SEQUENCE: 34
gctgcagact tcnttactc cnttaggttg tgaaagaccc          40

<210> SEQ ID NO 35
<211> LENGTH: 40
<212> TYPE: DNA
<213> ORGANISM: Macaca mulatta
<220> FEATURE:
<221> NAME/KEY: LTR
<222> LOCATION: (31)..(40)
<223> OTHER INFORMATION: The first 10 nucleotides of pLN 5'LTR
      (NCBI/GenBank: M28245)
<223> OTHER INFORMATION: n enspricht a, g, c or t/u

<400> SEQUENCE: 35
tttgncttta aantnannct nagaggtcaa tgaaagaccc          40

<210> SEQ ID NO 36
<211> LENGTH: 40
<212> TYPE: DNA
<213> ORGANISM: Macaca mulatta
<220> FEATURE:
<221> NAME/KEY: LTR
<222> LOCATION: (31)..(40)
<223> OTHER INFORMATION: The first 10 nucleotides of pLN 5'LTR
      (NCBI/GenBank: M28245)
<223> OTHER INFORMATION: n is a, g, c or t/u

<400> SEQUENCE: 36
tctctnnaag nttcnaggan gngnggggat tgaaagaccc          40

<210> SEQ ID NO 37
<211> LENGTH: 40
<212> TYPE: DNA
<213> ORGANISM: Macaca mulatta
<220> FEATURE:
<221> NAME/KEY: LTR
<222> LOCATION: (31)..(40)
<223> OTHER INFORMATION: The first 10 nucleotides of pLN 5'LTR
      (NCBI/GenBank: M28245)
<223> OTHER INFORMATION: n is a, g, c or t/u

<400> SEQUENCE: 37
aaancnaagg gacaggctgn aaangaaccc tgaaagaccc          40

<210> SEQ ID NO 38
<211> LENGTH: 40
<212> TYPE: DNA
<213> ORGANISM: Macaca mulatta
<220> FEATURE:
<221> NAME/KEY: LTR
<222> LOCATION: (31)..(40)
<223> OTHER INFORMATION: The first 10 nucleotides of pLN 5'LTR
      (NCBI/GenBank: M28245)

<400> SEQUENCE: 38
ccagcatgag atccccgcgc tggaggatca tgaaagaccc          40

<210> SEQ ID NO 39
<211> LENGTH: 40
<212> TYPE: DNA
<213> ORGANISM: Macaca mulatta
<220> FEATURE:
<221> NAME/KEY: LTR
<222> LOCATION: (31)..(40)
<223> OTHER INFORMATION: The first 10 nucleotides of pLN 5'LTR
      (NCBI/GenBank: M28245)
<223> OTHER INFORMATION: n is a, g, c or t/u

<400> SEQUENCE: 39
aaaaanggcc nttttttngc tagcnaggnc tgaaagaccc                             40

<210> SEQ ID NO 40
<211> LENGTH: 40
<212> TYPE: DNA
<213> ORGANISM: Macaca mulatta
<220> FEATURE:
<221> NAME/KEY: LTR
<222> LOCATION: (31)..(40)
<223> OTHER INFORMATION: The first 10 nucleotides of pLN 5'LTR
      (NCBI/GenBank: M28245)
<223> OTHER INFORMATION: n is a, g, c or t/u

<400> SEQUENCE: 40
ntnttatttg ntcanctatt aagcggtttt tgaaagaccc                             40

<210> SEQ ID NO 41
<211> LENGTH: 40
<212> TYPE: DNA
<213> ORGANISM: Macaca mulatta
<220> FEATURE:
<221> NAME/KEY: LTR
<222> LOCATION: (31)..(40)
<223> OTHER INFORMATION: The first 10 nucleotides of pLN 5'LTR
      (NCBI/GenBank: M28245)
<223> OTHER INFORMATION: n is a, g, c or t/u

<400> SEQUENCE: 41
tctcaagggc accaacatgt aactgntggc tgaaagaccc                             40

<210> SEQ ID NO 42
<211> LENGTH: 40
<212> TYPE: DNA
<213> ORGANISM: Macaca mulatta
<220> FEATURE:
<221> NAME/KEY: LTR
<222> LOCATION: (31)..(40)
<223> OTHER INFORMATION: The first 10 nucleotides of pLN 5'LTR
      (NCBI/GenBank: M28245)
<223> OTHER INFORMATION: n is a, g, c or t/u

<400> SEQUENCE: 42
gncntctgng tnnccncgn gncagntnta tgaaagaccc                              40

<210> SEQ ID NO 43
<211> LENGTH: 40
<212> TYPE: DNA
<213> ORGANISM: Macaca mulatta
<220> FEATURE:
<221> NAME/KEY: LTR
<222> LOCATION: (31)..(40)
<223> OTHER INFORMATION: The first 10 nucleotides of pLN 5'LTR
      (NCBI/GenBank: M28245)
<223> OTHER INFORMATION: n is a, g, c or t/u

<400> SEQUENCE: 43
acactgaaaa ctccaaagat gctattntat tgaaagaccc                             40

<210> SEQ ID NO 44
<211> LENGTH: 37
<212> TYPE: DNA
<213> ORGANISM: Macaca mulatta
<220> FEATURE:

```
<221> NAME/KEY: LTR
<222> LOCATION: (28)..(37)
<223> OTHER INFORMATION: The first 10 nucleotides of pLN 5'LTR
      (NCBI/GenBank: M28245)
<223> OTHER INFORMATION: n is a, g, c or t/u

<400> SEQUENCE: 44
aatttagggn tcccnnnngg ntcgtnctga aagaccc                               37

<210> SEQ ID NO 45
<211> LENGTH: 41
<212> TYPE: DNA
<213> ORGANISM: Macaca mulatta
<220> FEATURE:
<221> NAME/KEY: LTR
<222> LOCATION: (32)..(41)
<223> OTHER INFORMATION: The first 10 nucleotides of pLN 5'LTR
      (NCBI/GenBank: M28245)
<223> OTHER INFORMATION: n is a, g, c or t/u

<400> SEQUENCE: 45
ttgtgggntn nngggcntnt tanggngttn atgaaagacc c                         41

<210> SEQ ID NO 46
<211> LENGTH: 41
<212> TYPE: DNA
<213> ORGANISM: Macaca mulatta
<220> FEATURE:
<221> NAME/KEY: LTR
<222> LOCATION: (32)..(41)
<223> OTHER INFORMATION: The first 10 nucleotides of pLN 5'LTR
      (NCBI/GenBank: M28245)

<400> SEQUENCE: 46
tgttttgttt ngttttgaga ctgagtcttg ctgaaagacc c                         41

<210> SEQ ID NO 47
<211> LENGTH: 42
<212> TYPE: DNA
<213> ORGANISM: Macaca mulatta
<220> FEATURE:
<221> NAME/KEY: LTR
<222> LOCATION: (33)..(42)
<223> OTHER INFORMATION: The first 10 nucleotides of pLN 5'LTR
      (NCBI/GenBank: M28245)
<223> OTHER INFORMATION: n is a, g, c or t/u

<400> SEQUENCE: 47
gangcnatca actangatga catacaaaat nttgaaagac cc                        42

<210> SEQ ID NO 48
<211> LENGTH: 42
<212> TYPE: DNA
<213> ORGANISM: Macaca mulatta
<220> FEATURE:
<221> NAME/KEY: LTR
<222> LOCATION: (33)..(42)
<223> OTHER INFORMATION: The first 10 nucleotides of pLN 5'LTR
      (NCBI/GenBank: M28245)
<223> OTHER INFORMATION: n is a, g, c or t/u

<400> SEQUENCE: 48
tttatacata ccctagtttg aggccgttan gctgaaagac cc                        42

<210> SEQ ID NO 49
<211> LENGTH: 41
<212> TYPE: DNA
<213> ORGANISM: Macaca mulatta
<220> FEATURE:
```

```
<221> NAME/KEY: LTR
<222> LOCATION: (32)..(41)
<223> OTHER INFORMATION: The first 10 nucleotides of pLN 5'LTR
      (NCBI/GenBank: M28245)
<223> OTHER INFORMATION: n is a, g, c or t/u

<400> SEQUENCE: 49
ggtccnntnt ttcgntccnn nnnntangtt atgaaagacc c                41

<210> SEQ ID NO 50
<211> LENGTH: 40
<212> TYPE: DNA
<213> ORGANISM: Macaca mulatta
<220> FEATURE:
<221> NAME/KEY: LTR
<222> LOCATION: (31)..(40)
<223> OTHER INFORMATION: The first 10 nucleotides of pLN 5'LTR
      (NCBI/GenBank: M28245)
<223> OTHER INFORMATION: n is a, g, c or t/u

<400> SEQUENCE: 50
gccncnggcn tnncantcnc tggnncgngg tgaaagaccc                  40
```